(12) United States Patent
Rosenblatt

(10) Patent No.: US 8,449,447 B2
(45) Date of Patent: May 28, 2013

(54) SYSTEM AND METHOD FOR TREATMENT OF ANAL INCONTINENCE AND PELVIC ORGAN PROLAPSE

(75) Inventor: Peter L. Rosenblatt, Newton, MA (US)

(73) Assignee: AMS Research Corporation, Minnetonka MNA ( * ) Notice: Subject to any disclaimer, the term of this patent is extended or adjusted under 35 U.S.C. 154(b) by 381 days.

(21) Appl. No.: 12/836,286

(22) Filed: Jul. 14, 2010

(65) Prior Publication Data

US 2010/0331609 A1    Dec. 30, 2010

Related U.S. Application Data

(63) Continuation of application No. 11/765,761, filed on Jun. 20, 2007, now Pat. No. 7,794,385, which is a continuation-in-part of application No. PCT/US2005/046201, filed on Dec. 20, 2005.

(60) Provisional application No. 60/673,878, filed on Apr. 22, 2005, provisional application No. 60/637,665, filed on Dec. 20, 2004, provisional application No. 60/868,850, filed on Dec. 6, 2006.

(51) Int. Cl.
*A61F 2/00* (2006.01)

(52) U.S. Cl.
USPC .......................................................... 600/30

(58) Field of Classification Search
USPC ........... 600/29–32, 37; 128/89–898, DIG. 25; 606/119, 148, 222–225
See application file for complete search history.

(56) References Cited

U.S. PATENT DOCUMENTS

| | | | |
|---|---|---|---|
| 3,789,828 A | 2/1974 | Schulte et al. | |
| 6,599,235 B2 | 7/2003 | Kovac | |
| 7,070,556 B2 | 7/2006 | Anderson et al. | |
| 7,070,558 B2 * | 7/2006 | Gellman et al. | 600/37 |
| 7,351,196 B2 | 4/2008 | Goldmann et al. | |
| 7,351,197 B2 | 4/2008 | Montpetit et al. | |
| 7,407,480 B2 | 8/2008 | Staskin et al. | |
| 7,722,527 B2 | 5/2010 | Bouchier et al. | |
| 7,766,926 B2 * | 8/2010 | Bosley et al. | 606/151 |
| 2004/0039453 A1 | 2/2004 | Anderson et al. | |
| 2004/0215054 A1 | 10/2004 | Siegel et al. | |
| 2009/0259092 A1 | 10/2009 | Ogdahl et al. | |
| 2011/0112357 A1 | 5/2011 | Chapman et al. | |

FOREIGN PATENT DOCUMENTS

| | | |
|---|---|---|
| EP | 0639355 | 2/1995 |
| FR | 2852817 | 10/2004 |

(Continued)

OTHER PUBLICATIONS

Supplementary Partial European Search Report, Application No. 05854848.8, Dated Jul. 27, 2009.

(Continued)

*Primary Examiner* — John Lacyk
(74) *Attorney, Agent, or Firm* — Barbara A. Wrigley; Oppenheimer Wolff & Donnelly, LLP

(57) ABSTRACT

Using a sling that includes a central portion and at least two arms extending from the central portion, a method of treating anal incontinence may include positioning the central portion posteriorly to the rectum and/or anus of a subject, and extending each arm of the sling to a respective obturator region. Using a sling having the same or similar structure, a method of treating pelvic organ prolapse may include positioning the central portion beneath the ano-rectum of a subject, and extending each arm of the sling to a respective thigh incision near the obturator region.

20 Claims, 13 Drawing Sheets

FOREIGN PATENT DOCUMENTS

| JP | 6-501627 | 2/1994 |
|---|---|---|
| WO | WO 92-06652 | 4/1992 |
| WO | WO03013392 | 2/2003 |
| WO | WO 2004-030746 | 4/2004 |

OTHER PUBLICATIONS

International Search Report for International Application No. PCT/US05/46201 dated Jun. 13, 2007.

Ahmed Shafik, "Puborectoplasty, New Technique for the Repair of Fecal Incontinence," Dig. Surg. 1991; 8:182-186.

Frederick L. Green, M.D., "Repair of Rectal Prolapse Using a Puborectal Sling Procedure," Arch. Surg., vol. 118, Apr. 1983; pp. 398-401.

Office Action issued by the Canadian Patent Office, dated Dec. 2, 2011, Serial No. 2591493; 3 pages.

Notice of Final Rejection—Japan Patent Application Serial No. 2007-547029, Dated Dec. 16, 2011, 8 pages (incl. 5 pages English translation).

* cited by examiner

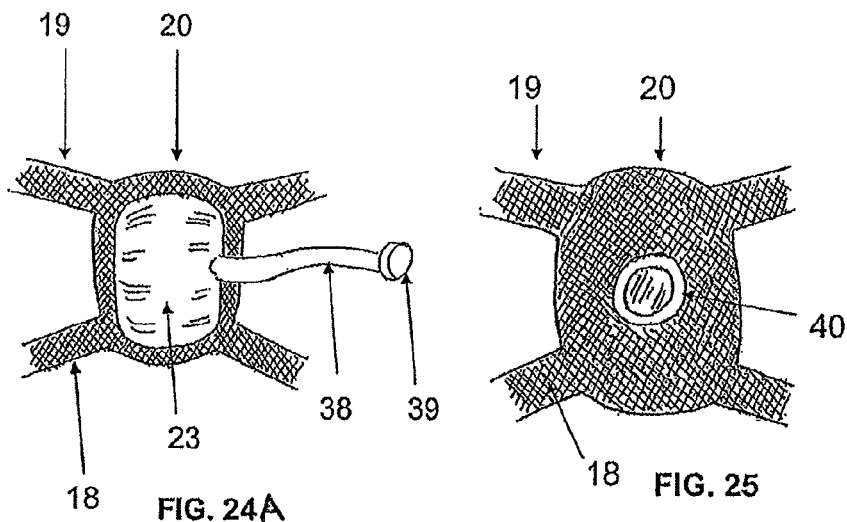
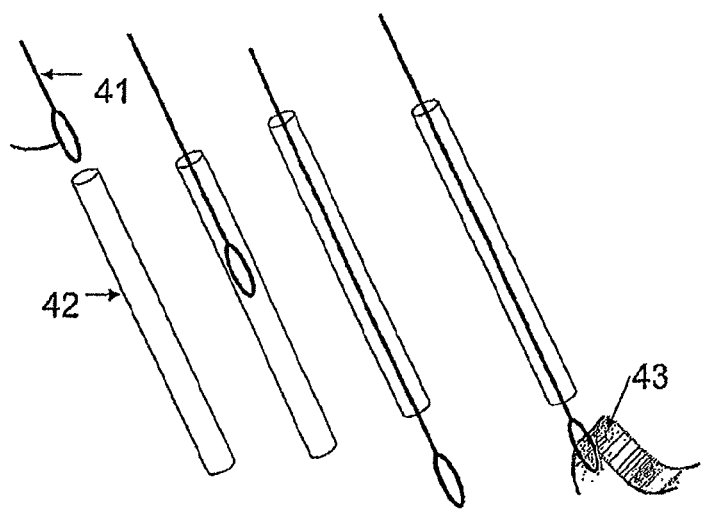
FIG. 26  FIG. 27  FIG. 28  FIG. 29

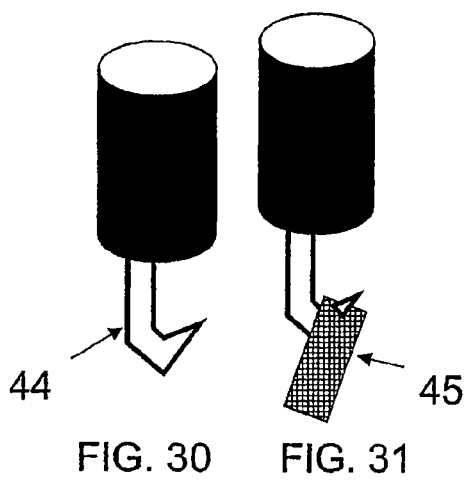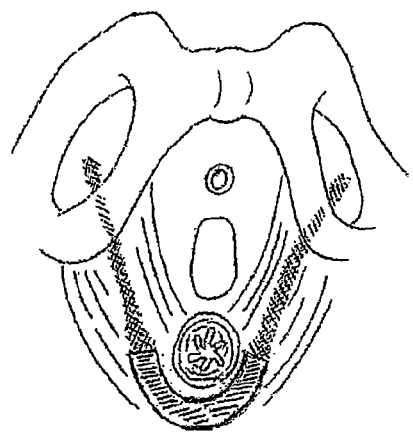
FIG. 30    FIG. 31
FIG. 32
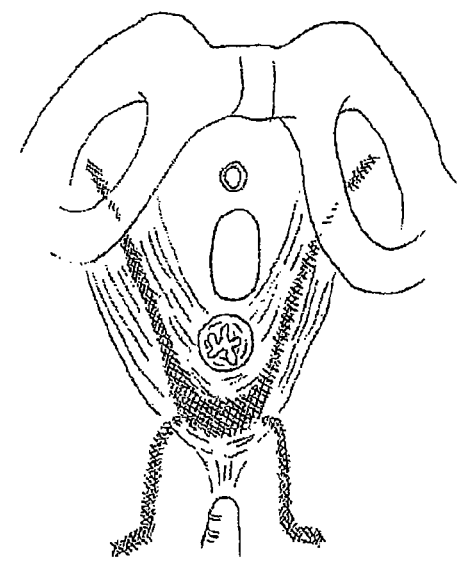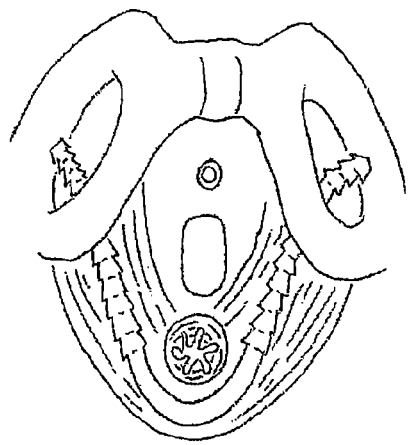
FIG. 33    FIG. 34

SYSTEM AND METHOD FOR TREATMENT OF ANAL INCONTINENCE AND PELVIC ORGAN PROLAPSE

CROSS REFERENCE TO RELATED APPLICATIONS

This application claims priority to and is a continuation of U.S. patent application Ser. No. 11/765,761, filed Jun. 20, 2007, which is a continuation-in-part of PCT Application No. PCT/US05/46201, filed Dec. 20, 2005, which claims the benefit of U.S. Provisional Application No. 60/637,665, filed Dec. 20, 2004 and also claims the benefit of U.S. Provisional Application No. 60/673,878, filed Apr. 22, 2005, the entireties of which are hereby incorporated by reference. This application also claims the benefit of U.S. Provisional Application No. 60/868,850, filed Dec. 6, 2006, the entirety of which is hereby incorporated by reference.

BACKGROUND OF THE INVENTION

Anal incontinence is a common problem that occurs in both men and women, though is certainly more prevalent in women after vaginal childbirth, presumably the result of trauma to pelvic floor muscles, supporting fascia and nerves. Fecal incontinence affects an estimated 7.6 percent of women between the ages of 30-90. The prevalence increases with age, affecting 3.6 percent of women between 30-39 and 15.2 percent of women between 80-90. Several factors contribute to anal continence, including the resting tone of the external and internal anal sphincters, as well as the position of the levator ani muscles, especially the puborectalis muscle, which forms a sling around the rectum and is responsible for the so-called "ano-rectal angle," which keeps stool in the rectum until voluntary defecation relaxes the puborectalis muscle and straightens the angle, allowing stool to move towards the anus.

Defecation is often aided by expulsive abdominal forces. Anal incontinence may occur as the result of several mechanisms, including direct damage to the internal or external anal sphincters (from iatrogenic episiotomy or spontaneous lacerations during vaginal delivery), or to the levator ani muscles. It may also result from indirect injury of these muscles through denervation of the nerves that supply these muscles. Treatment of this problem has centered on pelvic floor rehabilitation, dietary changes, or surgical correction. Surgery has been used to treat specific defects in the anal sphincters, such as external anal sphincteroplasty. Success rates of only 50% or less are generally reported for these procedures on long-term follow-up.

More recently, an artificial anal sphincter has been used to bypass these muscles, though this surgery involves fairly extensive dissection and requires the patient to depress a subcutaneous valve which temporarily deflates the sphincter cuff and allows voluntary defecation. This procedure is performed in very few centers in the U.S., and even in experienced hands, complications occur frequently. Dynamic graciloplasty, which involves mobilization and wrapping of the gracilis muscle around the anorectum is now another accepted procedure although is remains complex and requires extensive experience to obtain good results. More recently, sacral nerve stimulation has been used with some success to treat fecal incontinence, though the mechanism of success in these patients remains unclear, and may not be appropriate in women with obvious anatomic abnormalities, such as anal sphincter or levator muscle disruptions.

In addition, many women report other symptoms of bowel dysfunction, such as constipation and incomplete bowel emptying. For some women, these symptoms are due to either an anterior rectocele (a hernia of the rectum into the vaginal canal), or due to a defect in the levator ani muscles, which results in descent of the levator plate and/or perineum with abdominal straining. In addition, patients may be noted to have a defect in the posterior aspect of the rectum, or a posterior rectocele. There are very few treatment options for this condition, though retrorectal levatorplasty has been used in the past. In this procedure, an incision is made between the anus and the coccyx and the levator muscles are exposed bilaterally. Sutures are then placed in the levator muscles to plicate them together in the midline.

Pelvic organ prolapse is a condition where organs, such as the uterus, the rectum, or the bladder, fall down or slip out of place within a person's body. It is commonly used in reference to organs protruding through a woman's vagina, but prolapse may occur within men as well. In general, the levator ani muscles provide the main support for pelvic organs including, for example, the rectum, the vagina, and the urethra. In a person with a normal pelvis, the levator ani muscles keep the pelvic floor closed, thereby allowing the pelvic and abdominal organs to rest on the levator ani muscles. This also significantly reduces the tension that would otherwise be placed on the fascia and ligaments that support the pelvic organs. The posterior portion of the levator ani muscles arise from the area of the tendinous arch. The anterior portion of the levator ani muscles arise from the superior pubic rami and from the anterior end of the obturator internus muscles. This portion forms the pubococcygeus muscle and the puborectalis muscle. The pubococcygeus muscle is a generally thick, U-shaped muscle through which the urethra, vagina, and rectum transverse. The pubococcygeus muscle supports these structures at rest, and helps to augment the endopelvic fascia during coughing or straining. The puborectalis muscle is structured to act as a sling support for the rectum, and includes two ends that attach to the anterior side of the symphysis pubis. The levator ani muscle group includes an opening through which the vagina and urethra pass, which is referred to as the urogenital hiatus. Similarly, the levator ani muscle group includes an opening through which the rectum passes, which is referred to as the rectal hiatus.

In a normal woman, the pelvic floor muscles support most of the weight of the pelvic organs, such as the vagina, uterus, bladder, and rectum. Additionally, the various pelvic fascia and ligaments stabilize these structures in position. When the normal anatomic relationships in the pelvis are disrupted, or if injuries occur, dysfunctions such as urinary incontinence, fecal incontinence, or prolapse of the pelvic organs, may occur. For example, if one of the levator ani muscles is damaged, the muscle may be unable to adequately support the weight of the pelvic organs. This will result in a disproportionate amount of the pelvic organ weight being placed onto the pelvic ligaments, which are significantly weaker than the fibrous tissue of the ligaments that connect bones. In particular, the pelvic ligaments are more accurately described as thickening of the endopelvic fascia tissue, which is composed of collagen, smooth muscle, elastin, and fibrovascular bundles. These ligaments are not designed to carry the increased load resulting from problems in the pelvic floor. As a result, these ligaments may eventually fail. The failure or damage to the pelvic floor ligaments may cause, for example, the bladder, rectum, or uterus to prolapse through the vagina. Similarly, expansion of or damage to the levator or rectal hiatus may result in the bladder, vagina, or rectum prolapsing through the hiatus.

As stated previously, pelvic prolapse conditions result from the weakness or damage to the normal pelvic-support systems. In general, the main categories of pelvic prolapse include cystocele, rectocele, enterocele, uterine prolapse, and vaginal vault prolapse. The most common causes of these pelvic floor disorders in a female patient include child birth and removal of the uterus (hysterectomy). However, other contributing factors may include connective tissue defects, prolonged heavy physical labor, postmenopausal atrophy, neurogenic weakness of muscles, muscle weakness due to aging, and obesity.

A cystocele occurs when damage to the pubocervical fascia in the central or lateral areas (or both) allows the bladder to protrude into the vagina. Simply defined, a cystocele is a protrusion of the bladder into the vagina due to defects in pelvic support.

A rectocele is a bulge into the vagina caused by the rectum prolapsing through an attenuated rectovaginal septum. A rectocele is commonly a result of childbirth or chronic constipation. During childbirth, the rectovaginal septum and surrounding vaginal tissues are stretched and disrupted, which may cause weakness and stretching in these tissues. A rectocele typically forms a pocket just above the anal sphincter where stool may become trapped.

An enterocele is essentially a herniation of the small bowel into the vagina. Specifically, the peritoneal sac containing a portion of the small bowel extends into the rectovaginal space between the posterior surface of the vagina and the anterior surface of the rectum.

A uterine prolapse is the distention of the uterus and cervix outside the vagina. It is often associated with a rectocele, cystocele, or entrocele.

Finally, a vaginal vault prolapse is the distention of the vaginal apex after hysterectomy outside the vagina. It is also often associated with a rectocele, cystocele, or entrocele.

BRIEF SUMMARY OF THE INVENTION

The present disclosure describes systems and methods for treating anal incontinence, and other types of defecatory dysfunction, such as perineal descent, constipation, incomplete bowel emptying, and rectal prolapse. The present disclosure also describes systems and methods for treating pelvic organ prolapse and other pelvic floor disorders. Some disclosed systems and methods particularly facilitate minimally-invasive treatment of anal incontinence and pelvic organ prolapse.

BRIEF DESCRIPTION OF THE DRAWINGS

FIGS. 23-25 depict exemplary slings having fluid-filled sacs.

FIGS. 26-29 depict an exemplary use of a stylet having a loop.

FIGS. 30-31 depict an exemplary use of a stylet having a hook.

FIGS. 32-38 depict additional exemplary embodiments of slings.

DETAILED DESCRIPTION OF THE INVENTION

Figure 1:
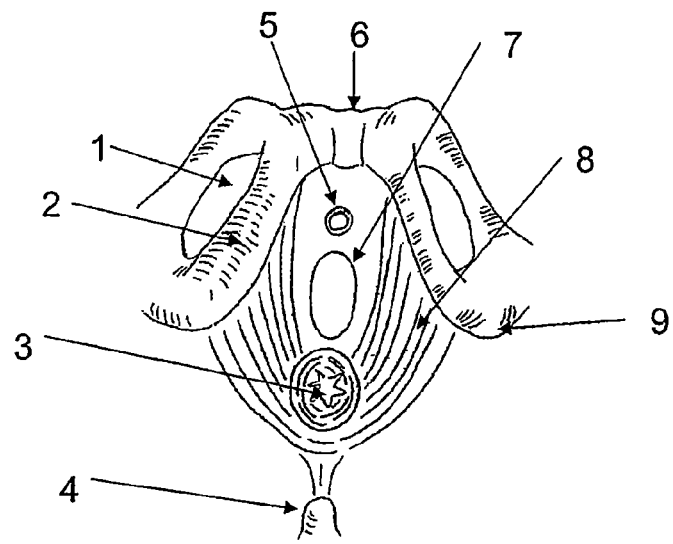
FIG. 1 depicts the anatomy of the bony pelvis.

The present disclosure provides a variety of systems and methods for treating anal incontinence. The normal ano-rectal angle can be restored by inserting a disclosed device under the posterior rectum, which may be supported with a synthetic or natural material in a sling-like position behind the anus and/or rectum. A posterior supporting apparatus may provide partial or complete closure of the rectum and/or anus with the posterior supporting apparatus.

In one embodiment, a synthetic or natural sling material may be placed under the rectum and may be supported by its arms, which may be extended up in a sling-like fashion through the obturator foramen bilaterally, or retropubically to the suprapubic region. In another embodiment, the device placed posterior to the rectum may include an inflatable or fluid-filled sac, which may or may not be adjusted post-operatively, by either changing its position or by altering the amount of fluid material, for example saline or a hydrogel, within the sac. "Fluid" is understood to include gasses, liquids, and semisolid media (such as gels). In some embodiments, the central portion of the sling may have a curved shape, such as a saddle shape, to help it conform to the external contour of the anus, rectum, ano-rectal angle, and/or levator ani muscles.

In one embodiment of a method of treating anal incontinence, an incision may be made between the anus and the coccyx and dissection performed, whereby the levator muscles and the levator plate are exposed. A small nick may be made on the medial thigh just lateral to the ischiopubic ramus and an introducer needle may be placed through the medial thigh incision, around the ischiopubic ramus, and be directed posteriorly into the ischiorectal fossa. The needle may then be directed lateral to the levator muscles, optionally with the assistance of a surgeon palpating the instrument though the vagina. The needle may then be brought posterior to the rectum, exiting the incision that was made in the midline. Alternatively, the needle may be passed from the midline incision between the anus and coccyx to the medial thigh incision lateral to the ischiopubic ramis. In one embodiment, a suture may be threaded onto the eye of the needle, which in this case may be placed from the medial thigh to the incision between the anus and the coccyx, and may then be withdrawn through the tissue and held on the medial thigh. The procedure is repeated on the contralateral side. A synthetic (i.e., polypropylene, polyester, etc.) mesh (such as tension-free vaginal tape, TVT) or natural graft material may then be attached to each of the sutures coming from the midline incision, and the mesh may then be brought up through the medial thigh incisions by pulling up on the sutures.

The mesh may have a covering plastic sheath, which can facilitate passage through the tissues. The sheath may be removed when the sling is properly adjusted.

In another embodiment, the needle that is passed through the tissue may have a hollow sleeve or tube over it (e.g., made of plastic, metal, or the like), and after passage, the needle may be withdrawn through the tissue, leaving the hollow sleeve in place. A stylet (e.g., made of plastic, metal, or the like) may then be then placed in the tube. The stylet may have a connector, such as a hook or a loop, so that a length of supporting material, such as a synthetic mesh (e.g., made of polypropylene or the like) or a natural graft, may be attached to the stylet connector. Exemplary uses of stylets with hooks or loops are shown in FIGS. 26-31. Once this procedure is performed bilaterally, the supporting material may be positioned under the rectum and the tension on the arms of the sling are adjusted. If the sleeves or tubes are utilized, the mesh can be adjusted before withdrawing the sleeves or tubes.

In another embodiment, two passes of the needles can be made on each side, one approximately at the level of the medial superior portion of the obturator foramen, and the other several centimeters inferior and slightly more lateral (at the inferior portion of the obturator foramen). This permits two lengths of supporting material (also called "mesh" but not necessarily limited to mesh) to be brought up on each side. These mesh strips are attached to a central mesh that may be placed under the rectum, which may be a pre-formed mesh, or may be constructed by attaching the central mesh to the four mesh strips—two on each side. The subrectal portion may be synthetic mesh, or may be made of another material, such as an inflatable or fluid-filled polymer sac. The sub-rectal element provides support to the posterior anus and/or rectum, and creates an angle between the anus and rectum, which keeps stool in the rectum until voluntary defecation.

In another embodiment, after the needle passes through the tissue, and is withdrawn, leaving a hollow tube in place, a plastic or metal stylet, previously fixed to the mesh with or without a sheath, can be placed up from the sub-rectal incision to the medial thigh incision and can be held. The mesh may then be brought up through the tubing by pulling on the stylet from above. Once the sling end comes out from the tubing, the hollow tube can be removed, after the sling has been adjusted for proper tensioning.

In another embodiment, the posterior aspect of the subrectal portion may be attached to the coccyx by one of several methods, such as direct suturing or with bone anchors. Such attachment can help maintain the position of the sub-rectal portion, which, in effect, restores the structure and function of the levator plate. Alternatively, the sub-rectal portion may have an extension coming off its inferior portion, which extends out and is fixed to the coccyx.

The fluid-filled sac under or adjacent to the rectum may have a port, such as a subcutaneous port, that may allow for fluid addition or removal in the post-operative period. This port may facilitate post-operative adjustment of the size and/or shape of the sac to provide for optimal results. The subcutaneous port may be placed directly under the sac, in the perineal skin, or may be connected to the sac by means of a connector tubing so that the port does not need to be located in the perineum itself, but instead may be positioned in a number of areas, including, for example, the buttocks.

The needle may have a hook near the end, that can be covered during insertion, but that may be exposed after the needle has been placed through the tissue. The user implanting the device may operate a switch or other actuator, such as a spring-loaded mechanism, to expose the hook. The arm of the sling, or a pre-loaded suture on the sling-arm, may then be placed on the hook and the needle withdrawn through the tissue.

In another embodiment, once the needle is placed through the tissue, the tip of the needle may be unscrewed off the end of the needle shaft. The arms of the sling may have a device attached to each end that may screw onto the needle shaft or otherwise fasten onto the needle shaft and then the needle is withdrawn, bringing the sling arm through the tissue.

A sheath covering the needle may remain in place in order to facilitate the movement of the synthetic material through the tissue, which is only removed once the tension on the sling is adjusted. The sheath may be deformable, rather than rigid or semi-rigid, and may be flattened after removal of the needle, to accommodate the flat shape of the sling material itself.

The needle could have blunt metallic insert (to maintain the strength of the needle) with a plastic covering sheath that has a sharp needle tip configuration on the end. After the needle is placed through the tissue, the metallic blunt needle is withdrawn, and the plastic needle tip cut off. A suture retriever is then placed anterograde through the hollow plastic tube and grasps a suture that has been attached or pre-attached to the sling. The sling is withdrawn through the plastic tube and the tube is removed once the sling is adjusted.

In another embodiment, the needle tip may be made from two separate pieces that act as jaws that open to catch the mesh or suture attached to the mesh, after the needle is passed through the tissue from the medial thigh to the incision posterior to the anus. This needle may be introduced with a plastic outer covering, so that the sling material may be drawn up through the tissue without catching on the surrounding structures. Once in proper position, the surgeon may remove the plastic sheath, which would then allow for the synthetic mesh to become fixed in the tissues.

A curved metal needle may be placed through the tissue from the medial thigh to the perineal incision. The end of the needle may be unscrewed, and the sling with attached plastic or metal piece may be screwed or snapped onto or into the connector on the needle. The sling, possibly with covering sheath, may then be withdrawn through the tissue and held and the plastic sheath is removed after the sling has been adjusted.

The shape of the sling may be a fixed width throughout its length. Alternatively, the central portion that is positioned under/behind the rectum may be wider than the arms. The central portion may be curved to help it conform to the shape of the tissue it is supporting. The curved shape may be a saddle shape, such as roughly a hyperbolic paraboloid or resembling a PRINGLES® brand potato crisp. The central portion may be preformed with the curved shape.

The mesh may be continuous throughout the length of the sling, or may have a central portion that includes a fluid-filled sac that is affixed to the sling arms on the sides. Preferably, the synthetic mesh would be continuous throughout its length in order to provide a backboard of support under the rectum and under the fluid-filled sac, if the fluid-filled sac is employed.

The fluid sac may have a circular or elongated shape under the rectum, or may include several compartments that can be separately filled with several access ports, in order to change the occlusion of the rectum. The fluid filled sac may have the curved shapes as discussed above.

Wings may connect a sling central portion to the arms of the sling. The wings may be made of mesh or other supporting material.

In another embodiment, the sling may be a hybrid of materials, comprised of, for instance, a polypropylene mesh along the arms of the sling in order to have self-attaching properties to the obturator fascia, and a natural xenograft material, such as porcine small intestinal submucosa, or an allograft, such as cadaveric fascia, located under and or lateral to the anus/rectum.

In another embodiment, the arms of the sling may include a synthetic material such as silastic or other plastic, and may have serrations that grab on to the obturator fascia as the arms are pulled through the tissue.

In another embodiment, the arms of the sling include sutures. There may be several sets of sutures on each side, in order to prevent the sub-rectal portion of the sling from rolling up underneath the anorectum.

In another embodiment, the arms of the sling may be attached to pelvic bone, such as the inferior-medial portion of the ischiopubic rami, or the inferior portion of the pubis, with bone anchors, suture material, or other fixation devices.

In another embodiment, the material under and/or lateral to the ano-rectum includes a synthetic material, such as silastic or other plastic material, that may be flexible, to conform to the shape of the bowel.

In another embodiment, a number of synthetic or natural elements are attached to the mesh in a direction transverse to the length of the sling, such as perpendicular or substantially perpendicular to the length of the sling. The elements may be semi-rigid and may be so positioned in the mesh as to be located under or lateral to the bowel when the mesh is deployed, for the purpose of keeping the mesh from rolling up underneath the anorectum. For example, the graft may have a stiff or flexible bar incorporated into the graft, located on either side of the rectum, to prevent rolling of the graft material.

In another embodiment, the sling may have additional straps attached to the subrectal portion that penetrate posteriorly, such as on either side of the coccyx, that may pass through the subcutaneous tissue and hold the graft in position, to prevent rolling of the subrectal mesh.

In another embodiment, the synthetic material may be elastic, which may permit stretching of the sling with abdominal straining, such as occurs with voluntary defecation.

In another technique, the sling may be passed through the levator ani muscle, rather than behind the muscles.

In another embodiment, the system may include a device used to evaluate the anorectal angle, for pre-operative diagnosis, intra-operative adjustment, and/or post-operative evaluation. The device is sufficiently flexible that it can be flexed to conform to the anorectal angle. The amount of flexion may be measured, thereby establishing the shape of the ano-rectal angle. In one embodiment, the device may be inserted into the rectum and has a flexible joint which is placed at the junction between the anus and rectum. The device may then measure the angle created between the rectal and anal portions, and this angle may be displayed visually on the device, in one of a number of manners, including a dial or a digital display. The angle may also be communicated to an external display for convenience. The device may include a rotation- or position-sensitive transducer. This ano-rectal angle measurement device may be adapted so that is fits over the examiner's gloved finger with a portion that fits over or on the examiner's distal finger, and another portion that fits over or on the proximal finger. In this manner, when the examiner bends his or her finger to determine the ano-rectal angle, the measured angle is recorded visually on a display.

Various portions of the device may be coated, impregnated, or formed with one or more drugs to be eluted to an adjacent tissue. Various portions of the device may be formed of biodegradable or bioabsorbable material.

FIG. 1 shows the anatomy of the bony pelvis, with the pubic symphysis (6), the ischiopubic ramus (2), the ischial tuberosity (9), the coccyx (4), and the obturator foramen (I). It also demonstrates the relationship of the levator ani muscles (and, in particular, the puborectalis (8)) to the urethra (5), vagina (7), and rectum (3).

Figure 2:
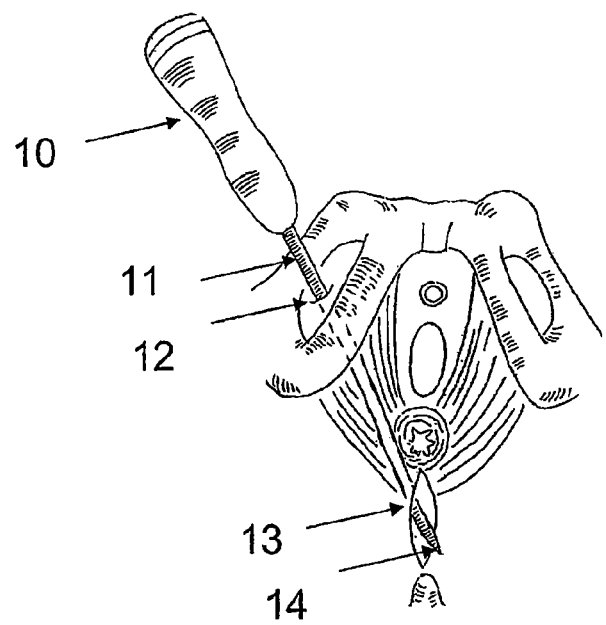
FIG. 2 depicts an exemplary placement of a device in the pelvis.

FIG. 2 demonstrates the placement of a needle (11) and attached handle (10) from the medial thigh incision (12), through the obturator membrane, into the ischiorectal fossa, and the needle tip (14) emerging through the vertical incision (13) between the anus and the coccyx.

Figure 3:
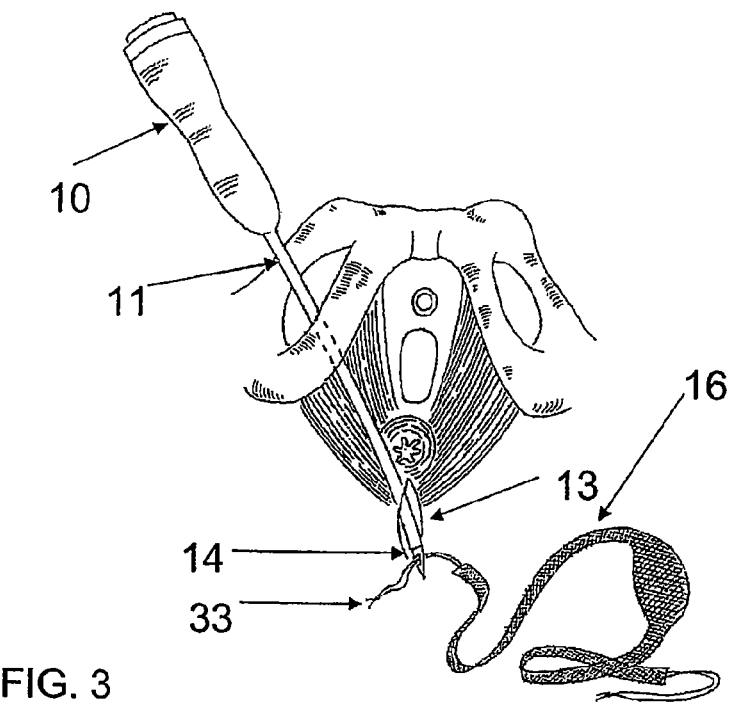
FIGS. 3-4 depict steps in one exemplary placement method.
Figure 4:
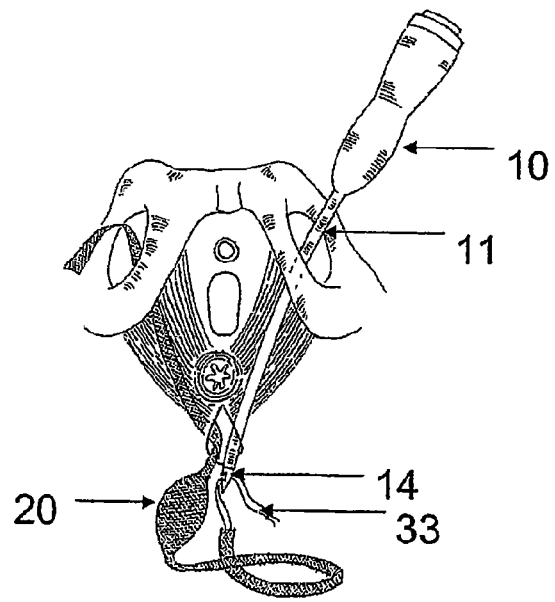

FIGS. 3-4 depict steps in one exemplary placement method. In FIG. 3, the needle (11) with the attached handle (10) has been placed through the thigh incision and through the obturator foramen, through the ischio-rectal fossa and out through the incision (13) between the anus and the coccyx. A suture loop (33) attached to the sling (16) is grasped by the needle tip (14) in order to transfer the sling to the thigh incision. FIG. 4 demonstrates the second pass of the needle on the contralateral side with the handle (10) and needle (11) in place. The tip (14) is grasping the suture loop (33) in order to pull the other arm of the sling up through to the thigh incision. This allows the central portion of the sling (20) to rest under the ano-rectal area.

Figure 5:
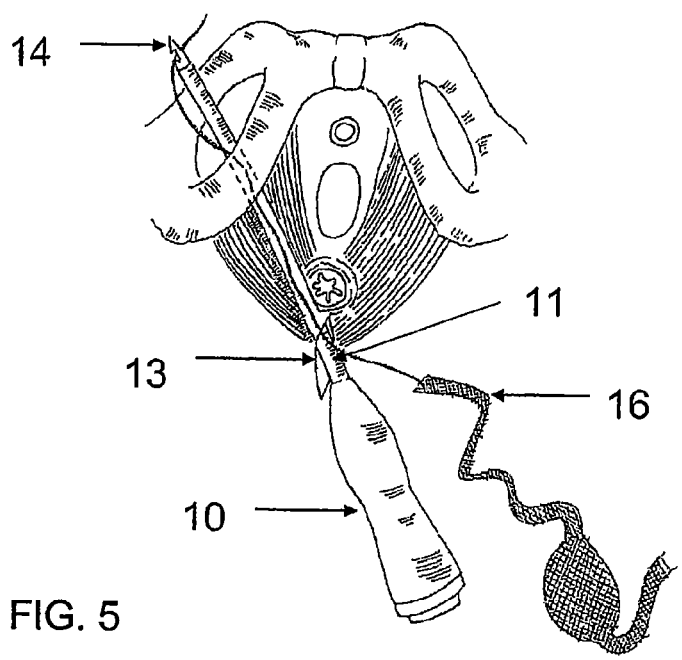
FIGS. 5-6 depict steps in another exemplary placement method.
Figure 6:
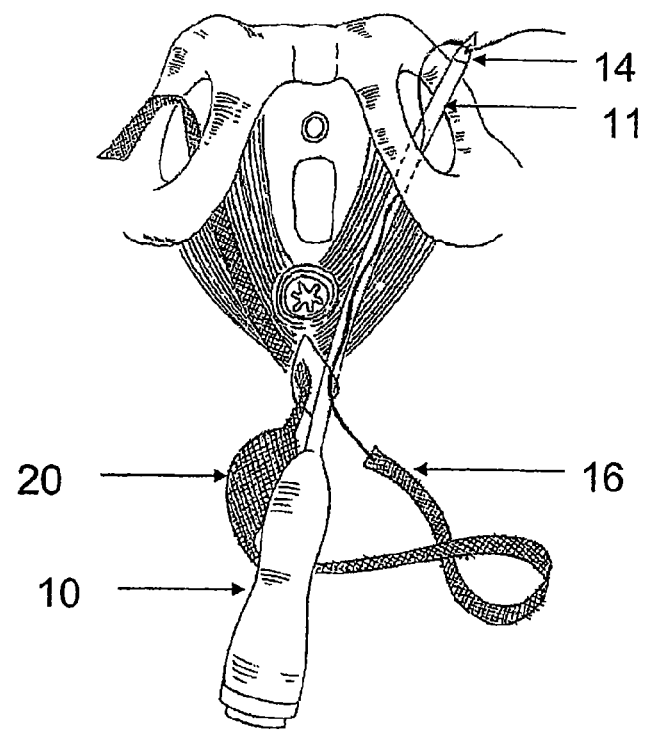

FIGS. 5-6 depict steps in another exemplary placement method. In FIG. 5, the needle (11) with attached handle (10) has been placed from the post-anal vertical incision (13) up through the ischiorectal fossa, through the obturator foramen, and out through the thigh incision, and has transferred a suture attached to the sling (18) to the thigh region. This allows the sling to be brought through the tissues up to the region of the thigh. FIG. 6 shows the right side of the sling in place and the needle (11) with attached handle (10) transferring a suture attached to the left side of the sling arm (16) up through the left side. The suture is being held by the needle tip (14).

Figure 7:
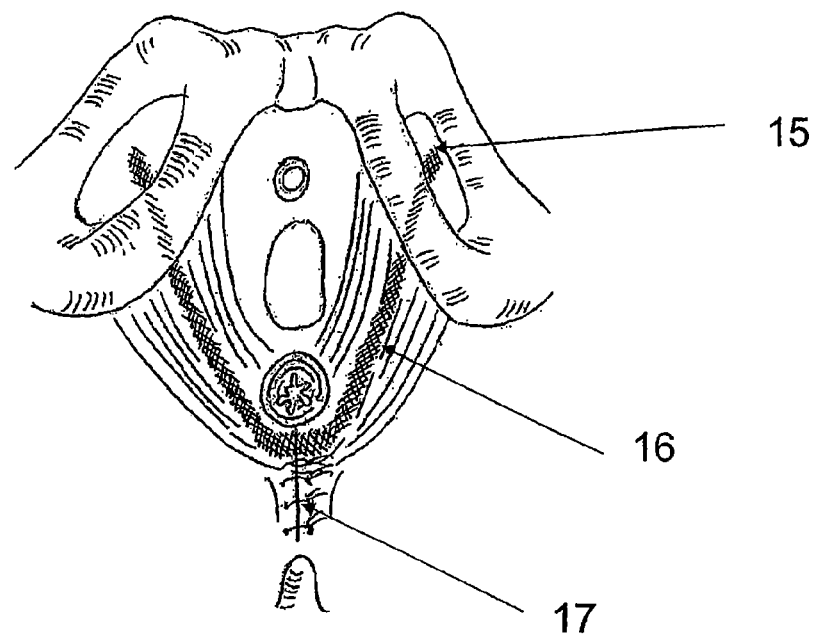
FIG. 7 depicts an exemplary final position of a length of supporting material.

FIG. 7 demonstrates a final position of the synthetic mesh (16) under the anus and/or rectum, with the incision between the anus and the coccyx (17), and up through the medial portion of the obturator membrane (15).

Figure 8:
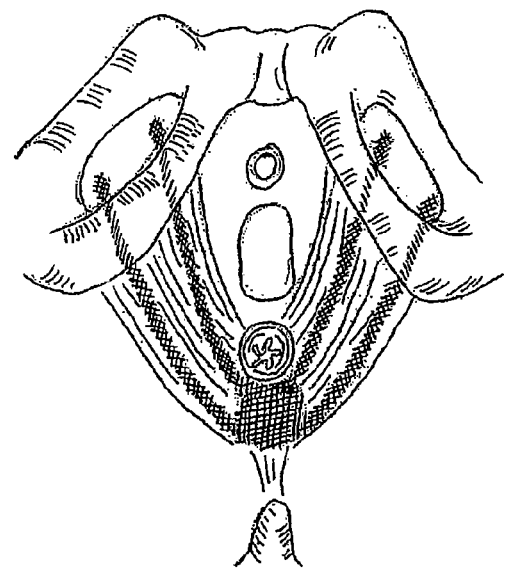
FIGS. 8-10 depict exemplary uses of two lengths of supporting material.

FIG. 8 demonstrates the use of two synthetic mesh straps placed through the obturator membrane, the first more distal and placed near the superior-medial aspect of the obturator foramen (18), and the second placed near the inferior portion of the obturator foramen (19), and attached to a central element (20).

Figure 9:
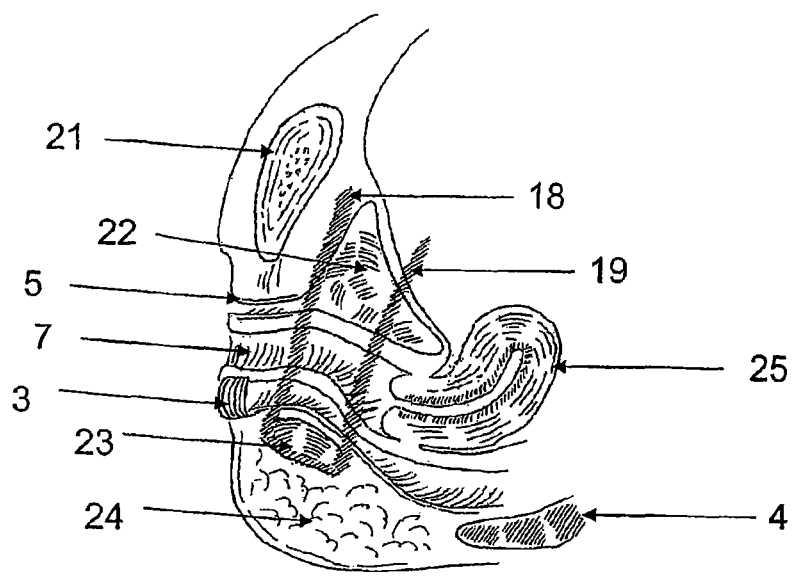

FIG. 9 shows a lateral orientation of the pelvis with the pubic symphysis (21), the bladder (22), the uterus (25), and the ischiorectal fossa (24) with two synthetic straps on each side, the first more distal (18) and the other more proximal (19), and a sub-rectal element (23) that includes a fluid or gas filled reservoir.

Figure 10:
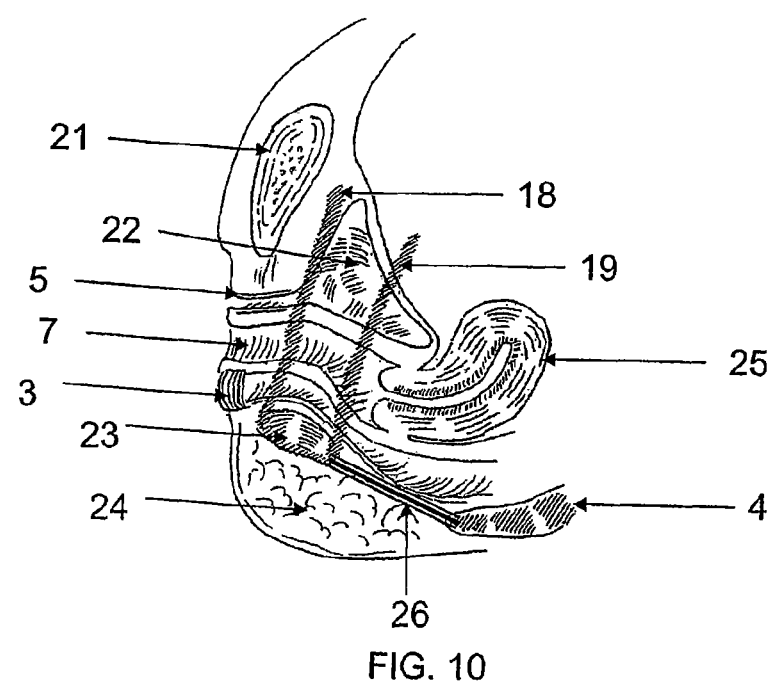

FIG. 10 shows a lateral orientation of the pelvis with the sling in place, with an extension (26) of the sub-rectal element attached to the coccyx with the use of sutures, bone anchor, or other method of affixing the synthetic material to the coccyx.

Figure 11:
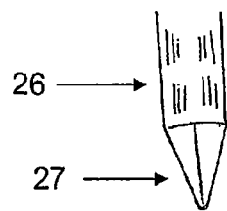
FIGS. 11-19 depict exemplary uses of various instruments to position a length of supporting material.
Figure 12:
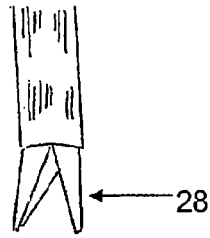
Figure 13:
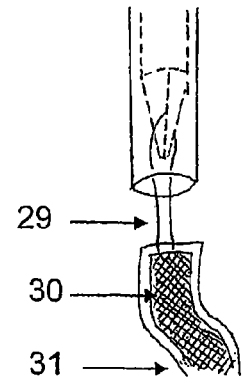

FIGS. 11-13 demonstrate the use of a needle (27) introducer placed from the medial thigh to the incision under of the rectum. Once through the tissue, the jaw opens in the middle, which reveals a grasping instrument (28) that can hold on to a suture (29) affixed to the mesh (30) with or without a plastic sheath (31). The sling material is then brought through the tissue, with or without a plastic outer tubing (26) through which the grasper had been placed during the needle insertion.

Figure 14:
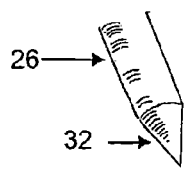
Figure 15:
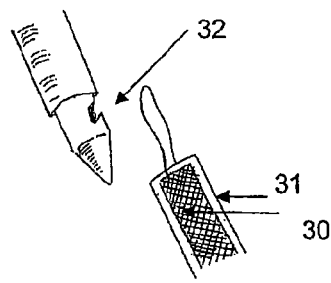
Figure 16:
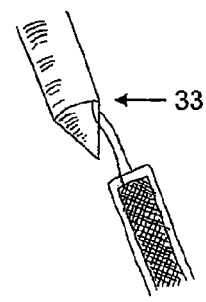
Figure 17:
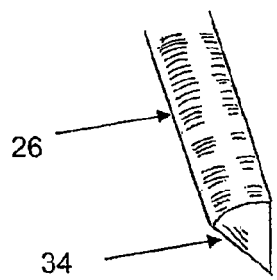
Figure 18:
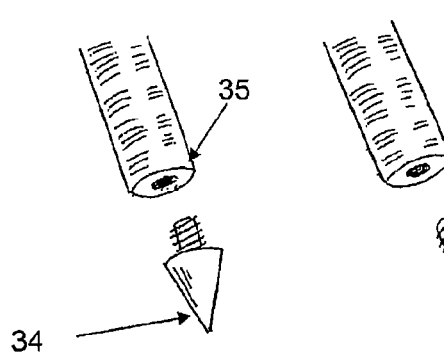
Figure 19:
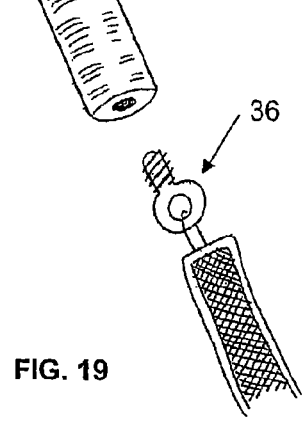

FIGS. 14-16 demonstrate a needle (32) that, after insertion through the tissue, can be advanced beyond the outer sheath, with or without a spring-mechanism to deploy the needle. This reveals a notch, on which the suture loop (previously attached to the mesh), can be placed (33), and the sling (30) is then brought up through the tissues to the medial thigh FIGS. 17-19 demonstrate a needle (34) that, after insertion through the tissue, may be separated from the shaft of the needle by unscrewing the needle tip. The sling would have a male-connector screw (36) that attaches to the straight needle shaft (35) and then the needle is withdrawn, which draws the mesh up through the tissue.

Figure 20:
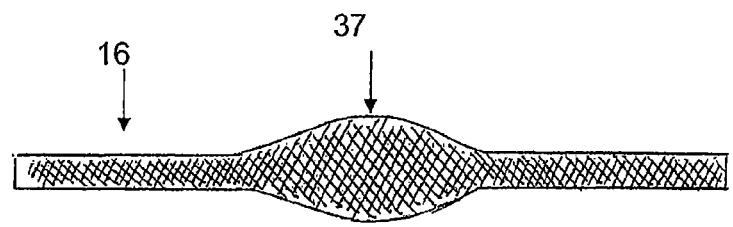
FIGS. 20-22 depict exemplary slings.
Figure 21:
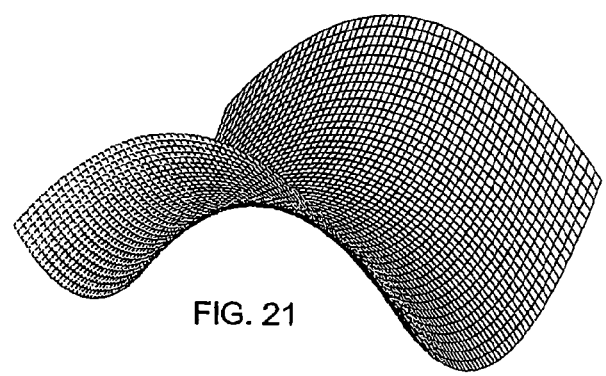
Figure 22:
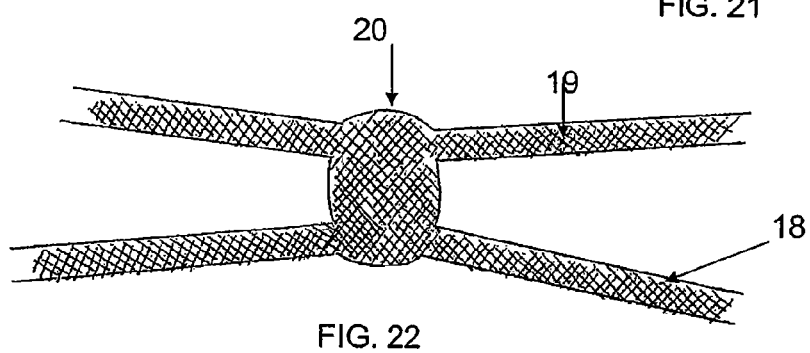
Figure 40:
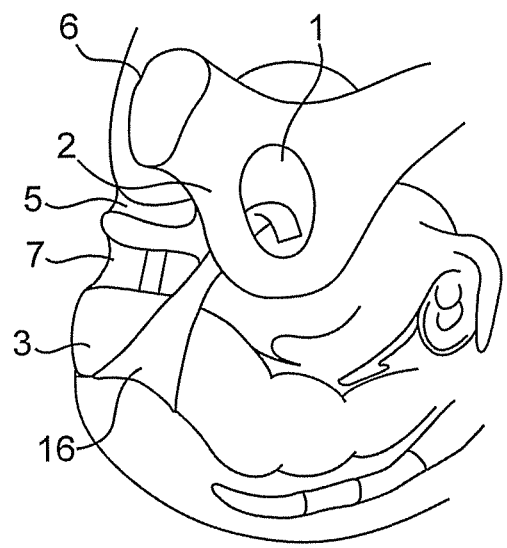
FIGS. 40-41 depict placement of a sling having a saddle-shaped central portion.
Figure 41:
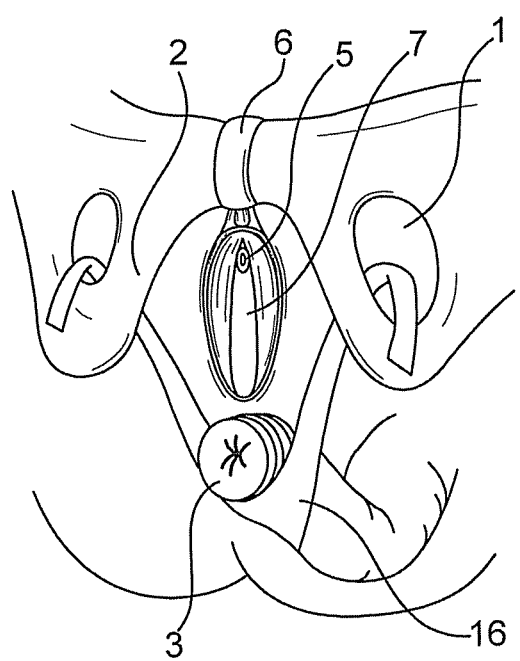

FIG. 20 demonstrates a sling that has narrow arms (16) and a wider area which would sit under the rectum (37) and distribute forces over a wide area. FIG. 21 illustrates a sling central portion (arms not shown) that has a curved shaped, specifically, a saddle shape. The saddle shape may facilitate making good contact with the anatomy to be supported. Its positioning is illustrated in FIGS. 40-41. One curve of the saddle allows the sling to arc between the obturator regions, while the other curve can complement the anorectal angle. FIG. 22 demonstrates an elongated central sling (20) with four attached arms, two of which are passed from the medial superior portion of the obturator membrane (18), and the other two which are passed through the inferior portion of the obturator membrane (19).

Figure 23:
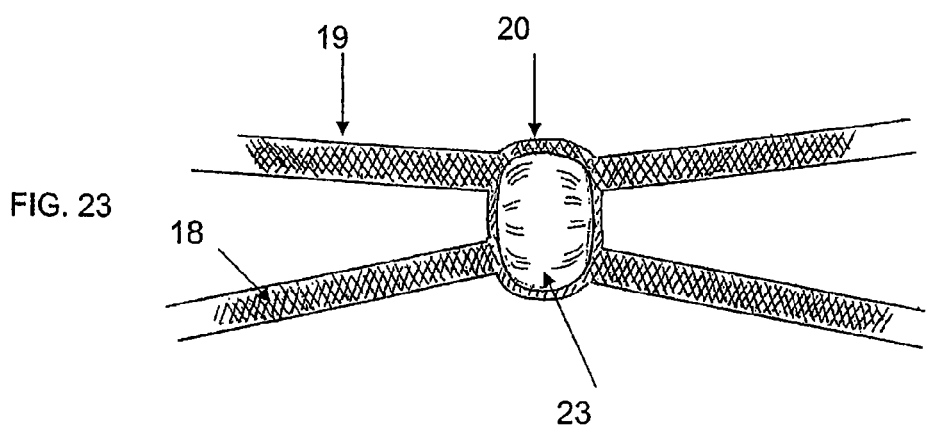

FIG. 23 demonstrates a superior view of a mesh that has a fluid-filled sac on the superior side of the graft material.

Figure 24:
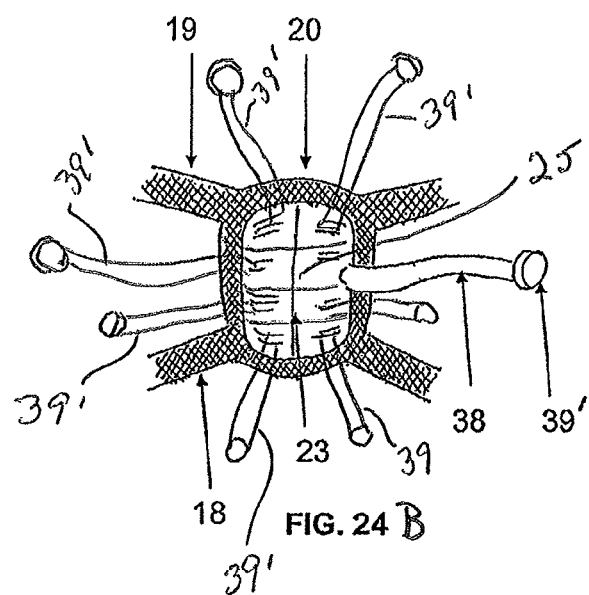

FIG. 24A shows another embodiment of a sling having a central portion 20 with an inflatable sac 23. Connector tubing 38 is attached to the fluid-filled sac 23 and can be placed under the buttocks or other location within the reach of the tubing, and has a port 39 at the end that can be used for filling or reducing the amount of fluid is contained within the sac. FIG. 24B shows another embodiment of a sling having a central portion 20 with an inflatable sac 23 having a plurality of inflatable compartments 25 that can be filled through a plurality of corresponding access ports 39'. While FIG. 24B depicts eight compartments and eight corresponding access ports, those of skill in the art will appreciate that any number of compartments and access ports may be utilized without departing from the spirit of the invention.

FIG. 25 demonstrates an inferior view of the central portion (20), which shows a port from the fluid-filled sac coming out through a hole at the bottom of the graft (40). This port may be accessed subcutaneously in order to either add more fluid or remove fluid.

FIGS. 26-29 exhibit an exemplary use of a loop stylet. Stylet (41) may be advanced through tube (42). A length of sling material (43) may be threaded through the loop so that the material catches in the loop. The stylet may then be withdrawn back through the tube to bring the end of the sling material to the desired position.

FIGS. 30-31 show an exemplary use of a hook stylet (44). A piece of sling material (45) may be stabbed onto a sharp tip of the hook. The hook may then be withdrawn through a tube to bring the end of the sling material to the desired location.

FIG. 32 shows a hybrid sling, comprised of, for instance, synthetic mesh arms attached to a central natural material placed under and/or lateral to the ano-rectum.

FIG. 33 shows the sling with additional straps of material that are attached to the subrectal portion of the device, and are secured in place by passage into subcutaneous tissue, in order to prevent rolling of the sling. The straps may be directed posteriorly, on either side of the coccyx, in order to keep the subrectal portion flat.

Figure 35:
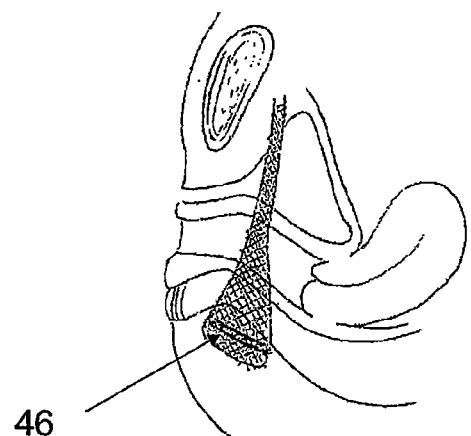
Figure 36:
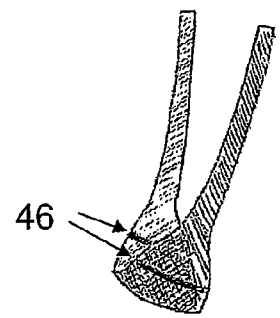
Figure 37:
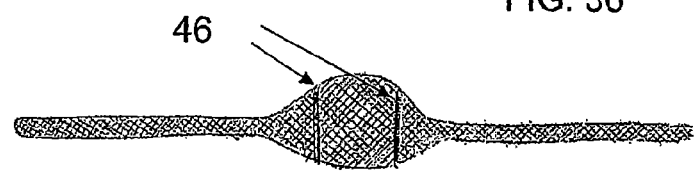

FIG. 34 demonstrates a sling made of a synthetic material such as silastic or other plastic with serrations on each arm that maintain the sling in position after adjustment by the surgeon FIGS. 35-37 show embodiments of slings that include rigid or semi-rigid elements (46). The elements may be attached to the sling in order to keep the sling from rolling under the ano-rectal portion.

Figure 38:
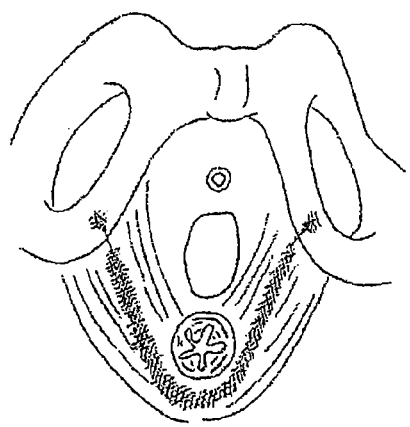

FIG. 38 shows the use of bone anchors to hold the sling into position, in this case to the inferior-medial portion of the ischiopubic rami.

Figure 39:
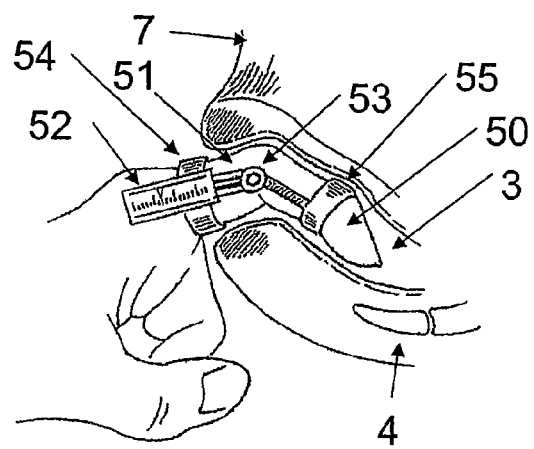
FIG. 39 depicts use of an exemplary device to measure the ano-rectal angle.

FIG. 39 depicts a device attached to the examiner's finger used to measure the angle between the rectum (3) and anus. The vagina (7) rests anterior to the anus and rectum, and the coccyx (4) is located posterior to the rectum. A proximal ring (54) is placed on the proximal phalanx (51) and the distal ring (55) is placed on the distal phalanx (50) and these are connected by a joint (53). The angle made between the anus and rectum is measured and displayed on a visual scale (52).

In one exemplary embodiment, a method to treat anal incontinence and/or defecatory dysfunction in a male or female may include:

placing an implant that passes under the anus and/or rectum and may pass under, over, or through the levator ani muscles; placing one of the ends of the implant through the obturator foramen and through an incision made in the medial thigh on the same side of the patient; and providing an elongate instrument that is used to transfer one end of the implant from the post-anal incision to a medial thigh incision, and then transferring the other end of the implant from the post-anal incision to the other medial thigh incision; or providing an elongate instrument that is used to transfer one end of the implant from a medial thigh incision to the post-anal incision, and then transferring the other end of the implant from the other medial thigh incision to the post-anal incision.

In another exemplary, a method of treating anal incontinence and/or defecatory dysfunction in a male or female patient may include:

creating an incision between the anus and the coccyx (vertical or horizontal);

creating an incision in the medial portion of each thigh;

providing an elongate instrument and an elongate implant for treating the condition;

passing one of the ends of the instrument between the post-anal incision, through an obturator foramen on one side of the patient, and the incision on the respective medial thigh;

associating the implant with the instrument;

using the instrument to pass the implant through the tissue between the postanal incision and one thigh incision such that the implant extends between the postanal incision, through the one obturator foramen, and one of the thigh incisions;

passing one of the ends of the same or another instrument between the postanal incision, through the other obturator foramen, and the other thigh incision; and using the instrument to extend the implant between the post-anal incision, through the other obturator foramen, to the other thigh incision such that the implant then extends from one thigh incision to the other thigh incision, through both obturator foramen and under the patient's rectum and/or anus (below or above the level of the levator ani muscles).

Various embodiments disclosed herein can be combined with one another to provide additional embodiments that include multiple features.

In another aspect of the present invention, the various slings and insertion needles described above in reference to the treatment of anal incontinence may be used in conjunction with a method for the treatment of pelvic organ prolapse. Pelvic organ prolapse is a condition where organs, such as the uterus, the rectum, or the bladder, fall down or slip out of place within a person's body. It is commonly used in reference to organs protruding through a woman's vagina, but prolapse may occur within men as well. In a normal woman, the pelvic floor muscles support most of the weight of the pelvic organs, such as the vagina, uterus, bladder, and rectum.

Additionally, the various pelvic fascia and ligaments stabilize these structures in position. When the normal anatomic relationships in the pelvis are disrupted, or if injuries occur, dysfunctions such as urinary incontinence, fecal incontinence, or prolapse of the pelvic organs, may occur. For example, if the levator ani muscle is damaged, the muscle may be unable to adequately support the weight of the pelvic organs. This will result in a disproportionate amount of the pelvic organ weight being placed onto the pelvic ligaments, which are significantly weaker than the fibrous tissue of the ligaments that connect bones. In particular, the pelvic ligaments are more accurately described as thickening of the endopelvic fascia tissue, which is composed of collagen, smooth muscle, elastin, and fibrovascular bundles. These ligaments are not designed to carry the increased load resulting from problems in the pelvic floor. As a result, these ligaments may eventually fail. The failure or damage to the pelvic floor ligaments may cause, for example, the bladder, rectum, or uterus to prolapse through the vagina. Similarly, expansion of or damage to the levator or rectal hiatus may result in the bladder, vagina, or rectum prolapsing through the hiatus.

Figure 42:
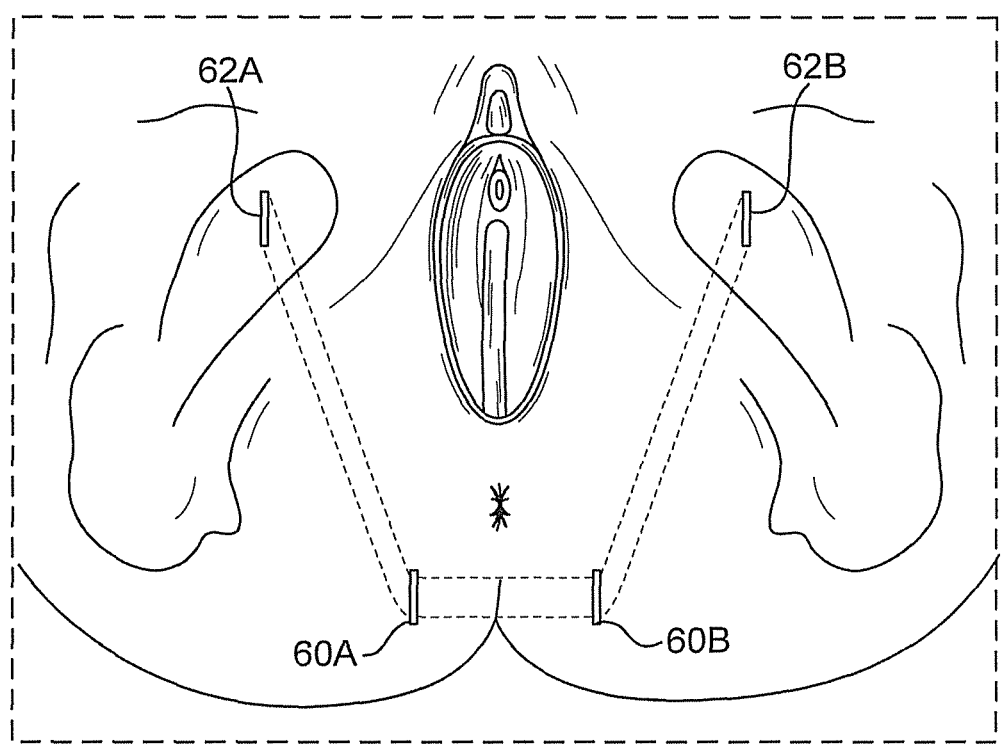
FIG. 42 generally depicts one exemplary method for treating pelvic organ prolapse according to the present invention.

FIG. 42 generally depicts one exemplary method for treating pelvic organ prolapse according to the present invention. The method begins at step 1 where a physician marks the location of four incisions on a patient's pelvic region. In particular, the physician marks two posterior incisions 60A and 60B and two thigh incisions 62A and 62B. The posterior incisions 60A and 60B may be located about 1.5 cm lateral and about 3 cm posterior to the mid-anus (midway between the anus and the coccyx). The two thigh incisions 62A and 62B may be, for example, at the level of the urethra along the descending pubic ramus.

The method continues at step 2 where the physician may inject a local anesthetic along a track from each thigh incision to the corresponding post-anal incision on the ipsilateral side, and between the two post-anal incisions. Then, in step 3, the physician uses a scalpel to make the two posterior incisions 60A and 60B, which may be approximately 1.5 cm in length. Next, in step 4, a small curved Kelly clamp or similar instrument is used to tunnel subcutaneously between the two posterior incisions 60A and 60B to create a space between the incisions, posterior to the anus. The physician may place a finger in the rectum to assist in guiding the clamp during the tunneling process. The method continues at step 5 where the physician inserts the clamp into posterior incision 60B and through posterior incision 60A, grasping an end portion of a sling arm or a connector on the sling. Thereafter, the physician pulls the sling through both incisions 60A and 60B until the central portion of the sling lies beneath the ano-rectum.

Then, in step 6, the physician makes a small stab incision over a first one of the thigh incision marks to create thigh incision 62A. An insertion needle (such as, for example, needle 11) is then inserted through thigh incision 62A in step 7 until it perforates the obturator membrane. The needle is tracked around the ischiopubic ramus with the handle portion of the needle generally parallel to the pelvic floor. The physician may use a finger to track the path of the needle down next to the vagina. Next, in step 8, the physician moves his finger to posterior incision 60A to track the needle out of the incision. The procedure continues at step 9 where the physician attaches the needle to the connector on the end of the sling arm protruding outward from posterior incision 60A and withdraws the needle back through the tissue and out through thigh incision 62A, pulling the sling arm to the desired location.

Next, in step 10, the physician makes a small stab incision over the second thigh incision mark to create thigh incision 62B. The insertion needle is then inserted through thigh incision 62B in step 11 until it perforates the obturator membrane. The needle is again tracked around the ischiopubic ramus with the handle portion of the needle generally parallel to the pelvic floor. Thereafter, in step 12, the physician moves his finger to posterior incision 60B to track the needle out of the incision. The procedure continues at step 13 where the physician attaches the needle to the connector on the end of the sling arm protruding outward from posterior incision 60B and withdraws the needle back through the tissue and out through thigh incision 62B, pulling the sling arm to the desired location. Once the physician has grasped and pulled both of the sling arms through the corresponding thigh incisions 62A and 62B, posterior incisions 60A and 60B may then be irrigated with an antibiotic solution and sutured in step 14.

Next, with a finger inserted into the rectum, the physician adjusts the sling arms in step 15 by grasping the excess portions of the arms protruding from thigh incisions 62A and 62B and pulling upward on both arms until gentle tension is palpable through the rectum. Then, keeping a finger in the rectum, the physician cuts the sling arms (as well as the sheath, if present) from the insertion needles and the sheaths are removed, leaving the sling mesh in place. The sling arms are then cut close to the patient's skin such that any excess portions of the sling arms protruding outward from the thigh incisions 62A and 62B are removed. The thigh incisions 62A and 62B are then irrigated with an antibiotic solution and subsequently sutured in step 16, thereby completing the pelvic floor treatment procedure. The sling, which may be constructed as a mesh formed from many materials such as, for example, polypropylene, adheres to internal body tissue without the need for additional sutures or attachment means.

One skilled in the art will appreciate that the procedure described above is merely one example of a method for treating pelvic organ prolapse according to the present invention. Thus, the steps described above may be modified or re-ordered without departing from the intended scope of the present invention. In addition, insertion needles and slings other than those shown and described above in reference to FIGS. 2-41 may be used along with the method of the present invention for treating pelvic organ prolapse. Furthermore, although the method was described with reference to the treatment of pelvic organ prolapse in a female patient, those skilled in the art will appreciate that a similar method may be used to treat pelvic organ prolapse in a male patient as well.

Although the present invention has been described with reference to preferred embodiments, workers skilled in the art will recognize that changes may be made in form and detail without departing from the spirit and scope of the invention.

What is claimed is:

1. A sling for use in treating anal incontinence comprising a central portion structured to be positioned posteriorly to the rectum and/or anus of a patient and attached to at least two arms extending therefrom, said central portion having a sub-rectal extension element extending therefrom that is sized and structured for attachment to a coccyx of the patient.

2. The sling of claim 1, wherein the central portion comprises an inflatable sac.

3. The sling of claim 2, wherein at least one arm is formed of mesh.

4. The sling of claim 2, wherein at least one arm is formed of tension-free vaginal tape.

5. The sling of claim 2, wherein at least one arm terminates with a filament.

6. The sling of claim 5, wherein the filament comprises a suture.

7. A sling comprising:
a central portion having a saddle shaped inflatable sac attached thereto, wherein the saddle shape is a hyperbolic paraboloid that defines a first preformed curve structured to allow the sling to arc between obturator regions and a second preformed curve structured to complement an ano-rectal angle of a patient, said central portion having a sub-rectal extension element extending therefrom that is sized and structured for attachment to a coccyx of the patient; and
at least two arms extending from the central portion, the arms formed of mesh or tension-free vaginal tape.

8. The sling of claim 7, wherein the inflatable sac further comprises an access port for inflating and/or deflating the sac.

9. The sling of claim 7, wherein the inflatable sac includes a plurality of compartments that are structured to be inflated separately through a corresponding plurality of access ports.

10. The sling of claim 2, wherein the inflatable sac further comprises a port for inflating and/or deflating the sac.

11. The sling of claim 1, wherein each of the arms includes serrations that are structured for maintaining the sling in position after implantation within a patient.

12. The sling of claim 1, further comprising at least one bone anchor associated with each arm for attaching the arms to respective portions of bone.

13. The sling of claim 1, wherein the central portion includes one or more anti-roll elements structured to prevent the central portion from rolling underneath the rectum and/or anus.

14. The sling of claim 13, wherein the one or more anti-roll elements are attached to the central portion in a direction that is substantially transverse to the length of the sling.

15. The sling of claim 1, wherein the sling arms are formed from a synthetic mesh material and the central portion is formed from a natural material.

16. The sling of claim 1 wherein said central portion has a hyperbolic paraboloid shape with first a second curves, said first curve configured to arc between obturator regions and said second curve configured to complement the patient's ano-rectal angle.

17. A sling for use in treating anal incontinence comprising a central portion attached to at least two arms extending therefrom, the central portion including a plurality of compartments that are structured to be inflated separately through a corresponding plurality of access ports, wherein said central portion includes a sub-rectal extension element extending therefrom that is sized and structured for attachment to a coccyx of the patient.

18. The sling of claim 17 wherein said central portion comprises an inflatable sac.

19. The sling of claim 18, wherein the sling includes four arms extending from the inflatable sac.

20. The sling of claim 18, wherein said sub-rectal extension element extends from the inflatable sac.

* * * * *